(12) United States Patent
Fundingsland et al.

(10) Patent No.: US 8,556,870 B2
(45) Date of Patent: Oct. 15, 2013

(54) DENTAL PACKAGE

(75) Inventors: Jon W. Fundingsland, Stillwater, MN (US); Marc Peuker, Schondorf (DE); Andreas Johannes Boehm, Reichling (DE); Timo K. Kuretzky, Kottgeisering (DE); Kevin Dale Foust, Dana Point, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 869 days.

(21) Appl. No.: 12/596,611

(22) PCT Filed: Apr. 1, 2008

(86) PCT No.: PCT/US2008/058981
§ 371 (c)(1),
(2), (4) Date: Mar. 1, 2010

(87) PCT Pub. No.: WO2008/130798
PCT Pub. Date: Oct. 30, 2008

(65) Prior Publication Data
US 2010/0175348 A1    Jul. 15, 2010

Related U.S. Application Data

(60) Provisional application No. 60/912,727, filed on Apr. 19, 2007.

(51) Int. Cl.
*A61M 35/00* (2006.01)
(52) U.S. Cl.
USPC .............................. 604/311; 433/90

(58) Field of Classification Search
USPC ............... 433/80, 89; 604/403, 310, 311; 206/221, 229, 277, 438
See application file for complete search history.

(56) References Cited

U.S. PATENT DOCUMENTS

| | | | |
|---|---|---|---|
| 6,099,307 | A | 8/2000 | Discko |
| 6,379,152 | B1 | 4/2002 | Dragan |
| 6,422,866 | B2 | 7/2002 | Dragan et al. |
| 6,524,103 | B1 | 2/2003 | Winkler et al. |
| 6,585,511 | B2 | 7/2003 | Dragan et al. |

FOREIGN PATENT DOCUMENTS

| | | |
|---|---|---|
| EP | 0 783 281 | 4/2002 |
| WO | WO 2006/132932 | 12/2006 |

OTHER PUBLICATIONS

Brochure entitled, "Filtek™ Z250 Universal Restorative" from 3M ESPE.
Brochure entitled, "Filtek™ Supreme Ultra Universal Restorative" from 3M ESPE.
International Search Report for International Application No. PCT/US2008/058981.

*Primary Examiner* — Melanie Hand
(74) *Attorney, Agent, or Firm* — Qiang Han; 3M Innovative Properties Company

(57) ABSTRACT

A dental package and a method of making such dental package for holding flowable dental material. The method comprising the steps of providing a container having an opening and providing first portion of a flowable dental material in the container. Further the method comprises hardening a predetermined second portion of the flowable dental material to form a closure that closes the opening. The invention provides for improved manufacturing and for facilitating the use of the package.

14 Claims, 5 Drawing Sheets

US 8,556,870 B2

DENTAL PACKAGE

CROSS REFERENCE TO RELATED APPLICATIONS

This application is a national stage filing under 35 U.S.C. 371 of PCT/US2008/058981, filed Apr. 1, 2008, which claims priority to U.S. Provisional Application No. 60/912,727, filed Apr. 19, 2007, the disclosures of both of which are incorporated by reference in their entirety herein.

The invention concerns a method of making a dental package for storing a flowable dental material. In particular, the method is related to providing flowable dental material in the package and hardening a portion of the material to form a closure for the package. Further, the invention relates to a package that contains a portion of such flowable dental material.

BACKGROUND OF THE INVENTION

In the field of dentistry, materials for treating a patient's teeth are often provided in packages that store the materials for a certain time period, for example over several months or even several years. Typically, such dental materials have to be stored in isolation from environmental influences, like moisture or air, for example, to prevent them from degrading or to prevent them from being contaminated. For that reason packages for dental materials are often hermetically sealed containers that the user may open to access the material. Such containers may be, for example, syringes or cartridges from which the dental materials can be dispensed.

A package of the type described usually includes a container for storing the dental material, and a discharge nozzle for directing the material to a desired place. A piston may be accommodated in the container, and when the piston is pushed forward it extrudes the material from the container through the nozzle. During storage, the container is typically sealed at one end by the piston, and at the other end by a cap. Alternatively, the container may comprise two or more dental materials, such as two or more components of a multi-component material separated in different chambers, and pistons accommodated in the respective chambers. The container may be used, for example, with a dispensing gun or device having a plunger or plungers for advancing the piston(s) within the container to dispense the material(s) in a desired location.

During manufacturing the containers are usually filled with the dental material and subsequently sealed by assembly of an appropriate closure, for example sealed with a cap and a piston. In recent years efforts have been undertaken to improve the assembly of parts, for example by improving the designs of the parts, because assembly often contributes a considerable portion of the container manufacturing costs.

Another area which has been the focus of developments in recent years is related to the filling packages with reduced inclusion of air with the dental material. This is because air included with the material stored in a package may cause the material to change, for example to harden or degrade. Furthermore, air, due to its compressibility, may cause dispensing inaccuracies and after-flow, for example, both of which cause difficulties for dental professionals. For example, WO 2006/132932 A1 discloses a system for storing and dispensing a material and a method for substantially air-free filling of a container with the material. The system comprises a container for storing an amount of a material, a piston and a front plug. The container comprises a vent that cooperates with the piston to allow air that is trapped in the container to escape. The piston together with the front plug are used to seal the material in the container.

Often the user needs to assess the optical characteristics of the material contained in the package prior to using the material, so that the optical characteristics of the material can be substantially matched to the appearance of the tooth to be restored. The optical characteristics include not only the color of the material, but also the translucency, for example. There are packages that include a part, such as a label, which is colored according to a color coding system to indicate the approximate optical characteristics of the material contained. Such system, for example, is based on individual colors that represent different optical shades of a dental material. The color system typically uses clearly distinguishable individual colors that provide for easy determination between different packages.

In EP 0 783 281 B1 a syringe system is disclosed for matching tooth composite colors to natural tooth color. The system includes a plurality of syringes. A part of each of the syringes carries a visible sample of the material contained in the syringe that is supposed to be compared to the color of a tooth.

Although some recently-developed packages offer advantages, there is still a need for a package that can be easily manufactured. In particular there is a desire to reduce the amount of parts required to make the package. There is also a desire to provide a method of making packages with a minimum number of assembly steps. Furthermore, there is still the need for minimizing the amount of air included in a package of dental material. In particular, there is a desire for that effect in combination with a package made of a minimum number of parts and/or assembly steps.

SUMMARY OF THE INVENTION

In a first aspect the invention concerns a method of making a dental package for holding flowable dental material. The method comprises the steps of:
  i. providing a container having an opening;
  ii. providing at least a first portion of a flowable dental material in the container;
  iii. hardening a predetermined second portion of the flowable dental material to form a closure that closes the opening.

The method may further comprise the step of providing at least a part of the second portion of the flowable dental material in the container. Alternatively the second portion may be provided at least partially onto the container.

In an embodiment of the invention the method of making a dental package for holding flowable dental material. The method comprises the steps of:
  i. providing a container having an opening;
  ii. providing a flowable dental material in the container;
  iii. hardening a predetermined portion of the flowable dental material to form a closure that closes the opening.

In an example a predetermined portion of the flowable material is related to filling the package with the contents of flowable material desired to be provided to a user plus a predetermined additional amount of flowable material that is used to form the closure.

Preferably the predetermined portion of the flowable dental material is hardened to form a non-flowable portion of the dental material and thereby a closure that closes the opening. In this regard the non-flowable material may include a material state of a higher viscosity relative to the flowable material.

The package may have a designated packaged content and a designated pre-packaged content. The designated packaged and pre-packaged contents are preferably determined by the manufacturer of the package. The pre-packaged content preferably corresponds to an amount of flowable dental material that is originally placed into and optionally partially onto the package by the manufacturer prior to hardening the predetermined portion of the material. Therefore, hardening of the predetermined portion of the material may result in maintaining an amount of flowable dental material in the container that substantially corresponds to the packaged content. For example, a new package typically contains an amount of flowable dental material that substantially corresponds or corresponds to the designated packaged content.

In a particular embodiment of the method of the invention, the method may further comprise the step of labeling the package with an indication of the weight or volume of the packaged content, wherein the packaged content substantially corresponds to the amount of flowable dental material contained in the package. Such labeling may be performed directly on the package or indirectly on a secondary packaging component, for example on a box containing the package or on a label. Indirect labeling may also include the designation of a fill volume provided by more than one package, for example, if several packages are provided in a kit the label may designate the sum of the individual packed contents of the packages as fill volume.

In another embodiment of a method of the invention, the step of hardening may involve exposing at least a part of the flowable dental material to light which causes the flowable dental material to polymerize. The light used for hardening preferably has a wavelength within a range of 430-480 nm, which substantially corresponds to visible violet to blue light. Preferably the light used for hardening includes wavelengths within a range of 430-480 nm. The light preferably has an intensity sufficient to harden the flowable dental material within a reasonable period of time. For example, an intensity within a range of 200 to 10000 mW/cm$^2$, preferably within a range of 5000 mW/cm$^2$ to 10000 mW/cm$^2$, would be likely to harden flowable dental material within 1 to 20 seconds under normal operating conditions. Such intensity values may for example be reached by plasma lamps.

Hardening may be a procedure including a definite step of polymerizing the material while exposing it to light, for example of mentioned wavelengths and intensities, and another definite step where the material further polymerizes in substantial absence of such light. Typically such further polymerization step in substantial absence of such light generally completely stops after a certain time and afterwards does not further continue into available flowable material.

The closure formed of the non-flowable portion of the dental material may comprise more cross-linked polymer chains, crystalline components or chemically reacted components than a flowable portion of the same material. In particular the molecules of the non-flowable portion preferably have an average molecular weight that is higher than the average molecular weight of the flowable portion of the same material. In this regard, the term "a flowable portion of the same material" means with respect to the present invention the material from which the non-flowable portion may be obtained, for example by polymerization.

A second aspect of the invention is related to a package having a container and an opening. The package may contain a flowable and a non-flowable portion of a dental material. Further, the non-flowable portion forms a closure member for the package, and preferably the package is made by the method according to the first aspect of the invention.

The closure preferably is adapted to provide a hermetic seal for the dental package, for example the closure may form a hermetic seal with the opening of the container. Preferably the closure, and more preferably in particular the non-flowable material, has a permanent material structure, meaning that, for example, it remains non-flowable during storage. Preferably the closure, and more preferably in particular the non-flowable material, is non-thermoplastic.

An embodiment of the second aspect is related to an alternative package comprising a container and a dental material. The container has an opening and contains a flowable portion of the dental material. The opening is closed by a closure member that is formed by a non-flowable portion of the dental material, wherein the closure member is a cap.

Preferably the cap, if provided, has an interior rim that is adapted to fit on an outside structure of the package. Such structure may for example be a nozzle having an opening, and the cap may be fitted with the rim onto the nozzle to hermetically seal the opening.

An embodiment of the second aspect is related to another alternative package comprising a container and a dental material. The container has an opening and contains a flowable portion of the dental material. The opening is closed by a closure member that is formed by a non-flowable portion of the dental material, wherein the closure member is a piston.

The piston preferably is adapted to be movably fitted in an inside structure of the package. For example, the piston may be received within the opening of the container and hermetically seal the opening, and may further be adapted to displace material stored in the container.

An embodiment of the second aspect is related to still another package comprising a container and a dental material, the container having an opening and containing a flowable portion of the dental material, wherein the opening is arranged within a side wall of the container and is closed by a closure member that is formed by a non-flowable portion of the dental material, and wherein the closure member is a plug.

The plug is preferably adapted to be non-movably fitted in an inside structure of the package. The plug may, for example, be received in the opening of the container and hermetically seal the opening. The plug may further be retained in the opening.

Preferably the dental material initially is flowable and the closure member is formed by hardening a predetermined portion of such dental material, to form a non-flowable dental material and leave a flowable portion of the dental material available for dispensation by a user.

In an embodiment of the invention the package comprises a container having a chamber for receiving dental material that opens at an outlet opening of the container. The chamber may further comprise a rear opening for receiving a piston. The package may further comprise a cap and a piston. Preferably the cap is used for closing the outlet opening. The piston may be used for closing the rear opening of the container, and for extruding material from container through the outlet opening. A cap or a piston or both may be formed by the non-flowable portion of the dental material.

In a particular embodiment a part of the non-flowable material is outside of the package and another part is inside the package. For example, a cap of a non-flowable material may be generally outside of the container, but a pin that is formed with the cap may extend into the outlet opening of the container. This may be of advantage because the pin may provide an additional seal for the container and therefore may provide for a longer shelf life of the package.

In another embodiment of the invention the flowable portion and the non-flowable portion are substantially continuous, meaning that both portions form a substantially continuous structure and are not spaced apart or separated by another structure or material. Preferably the flowable portion and the non-flowable portion are continuous, in particular may be in direct contact with one another. The flowable portion and the non-flowable portion may form a transition zone between one another. The transition zone may be an area within the material that comprises a substantially flowable material that over a certain distance transitions into a substantially non-flowable material, for example with the viscosity of the flowable material increasing from the flowable material area towards the non-flowable material area.

In a further embodiment of the invention the closure member forms an indicator. The indicator may indicate the color shade of the material. Further, the indicator may indicate the translucency of the material. Such an indicator may be used to assess the optical characteristics of the dental material, in particular the optical characteristics of the dental material when it is hardened. For example, a dentist who for a restoration desires to fill a cavity of a patient's tooth with dental filling material may use the indicator to choose the color or translucency of material, or both, that matches best with the tooth. He may pick up several different packages and compare the individual indicators of the packages with the patient's tooth to help chose the package whose material will match best when used to repair the tooth.

In a preferred embodiment, the indicator is integrally formed with the closure member. For example, the indicator and the cap may be formed as one piece.

In a particular embodiment the indicator resembles the shape of a human incisor (a front tooth). The indicator may also resemble the shape of a molar (a back tooth) or a premolar (a tooth between the back and front teeth). The shape of the tooth-shaped indicator may not be a perfect reproduction of a tooth but may reproduce certain characteristics, such as thicker portions in one area and a certain taper towards an end. Therefore a dentist may assess especially the color, the translucency and the appearance of the two in combination when selecting which packaged material to use for a restoration.

In another embodiment the indicator is formed by the cap. The cap may be designed so that the cap comprises dimensions that correspond to dimensions of a human tooth. Thereby, the cap itself may provide the color shade and/or translucency of the material stored in the container. For example the cap may have a tapered rim that has a thickness characteristic generally corresponding to an approximate thickness of a human tooth.

The flowable dental material as it is referred to within this specification is preferably a hardenable dental material. Further, the non-flowable dental material as it is referred to within this specification is preferably a hardened dental material.

In a particular embodiment the dental material is a light-curable dental material. The material may be based on derivatives of methacrylates, oxiranes, siloranes, or any other polymerizable monomeric or oligomeric resin. Such dental material may also include dual curable materials, for example materials that are chemically and light curable. The dental material may be a universal filler material like Filtek™ Supreme or the universal composite Filtek™ Z250 available from 3M ESPE. Further materials may be any dental filling materials, for example light-curing dental filling materials.

In another particular embodiment the package is designed to contain a single dose amount of flowable dental material, for example having a size suitable for storing an amount of material typically needed to restore a single tooth. The package design of the present invention may include parts that do not need to be reused, and therefore can be easy and inexpensive to manufacture. A package according to the present invention may also reduce waste from separate components, and may include materials that are environmentally friendly.

In another embodiment of the invention the package is at least in part is made by injection molding. Therefore, preferably the container is made of a plastic material. The package may comprise a cap, a plug, a piston or other parts that may be made of a plastic material other than a dental material. In particular the plastic materials used for parts of the package may be selected from among polycarbonate (PC), polystyrene (PS), polybutylene terephthalate (PBT), acrylonitrile butadiene styrene (ABS), polyoxymethylene (POM), polypropylene (PP), polyethylene (PE) and polyamide (PA).

The package of the invention may comprise a container in the form of a capsule, for example a dental capsule, a syringe, for example a dental composite syringe, or any other suitable form.

A third aspect of the invention is directed to a kit that comprises at least one package according to the invention and a tray or display for holding and providing the package. Preferably the kit comprises a plurality of packages of the invention. Preferably the kit also comprises a tray or display for holding and providing such a plurality of packages. The kit may also comprise a plurality of packages containing a material of a different color shade. Preferably the kit comprises at least one of each color shade out of a palette of different color shades. Therefore the user is allowed to conveniently select the desired color shade from a series of reference examples.

A fourth aspect of the invention is directed to the use of a dental material to form a closure member for a container for storing a flowable portion of the same dental material. The use of dental material to form a closure for a package may be advantageous because it may reduce the need for manufacturing additional parts and, for example in combination with a method of making the package of the invention, the assembly of those additional parts.

A fifth aspect of the invention is related to a system for packaging dental material, comprising a filler unit for dispensing dental material into a package and a light-emitting device for hardening that dental material. In particular such a system may provide for filling a package with dental material. The system may further have a feeder for supplying parts of the package, such as a container, a cap and/or a piston, to a location at which they would be assembled. The system may comprise a filling device, for example a dispensing device supplying the dental material to a specified location with a filling needle. The parts may be automatically handled within the system. For example a container may be fed into the system and placed relative to the filling device, and filled with the dental material. The container may be filled through an opening of the container, for example, through its open rear end or through an outlet opening at the front end. The container may be overfilled so that a portion of the dental material is available for hardening and forming a closure. In case the container is rear-end filled the material may, for example, be overfilled such that a portion of the dental material exits the outlet opening of the container, and that portion may be subsequently hardened to form a closure, for example a cap.

The material hardened to form a closure may also be provided alternatively. For example a first sub-portion of the dental material filled in the container may be hardened to form a piston which may then be used to force a second sub-portion of the dental material out through the outlet opening, and that second sub-portion may be hardened to form a cap.

The filling device may seal the opening through which the container is filled during filling. This may allow to force the material through another opening of the container during filling and prevent the material from escaping out of the opening through which the container is filled.

Hardening may be caused by exposing the flowable dental material to light provided by the light-emitting device. For example the cap may be exposed to light through a generally transparent or translucent mold that is used to provide the cap with a certain an outer shape. The piston may, for example, be exposed to light provided by the light-emitting device (or a second light-emitting device) through the open rear end of the container.

Upon removing the closure from the container the non-flowable material may separate from the flowable material within a transition zone. The separation line may for example be in a zone of material that is partially hardened so that the first material to be dispensed is the partially hardened material. Typically a user would discard such partially hardened material, for example on a pad, prior to dispensing the flowable material in a desired location.

The present invention is advantageous in that it provides an optimized method of making a package for a dental material. In particular, the invention may provide for saving assembly costs. Further, it may reduce the number of parts required to make the package. This is, for example, because the closure member may be directly made of the dental material contained in the package, and therefore pre-manufactured closures and their assembly may be unnecessary. Generally the package of the invention may be advantageous in that it provides a relatively long shelf life.

Furthermore, the invention may be advantageous in that it provides a method and a package allowing the package to be filled with minimal inclusion of air. Inclusion of air may be minimized because the invention generally allows the creation of a closure directly adjacent the material to be sealed in the container so that substantially no air is present between the closure and the material before and after closing of the package. This is in contrast to closures that are applied on a container and require the closure to be moved relative to the material in the container. In this case there may be air between the material and the closure which may be trapped in the container.

Another advantage may be provided by the invention in that it provides a package that may provide the optical characteristics of the material contained to a user, while at the same time being easy to manufacture. The package may allow the optical characteristics of the material contained therein to be assessed by a user, in particular without the need for opening of the package. It may in particular be advantageous that the optical characteristics be provided by an indicator that is formed by a non-flowable portion of the dental material and which forms a substantially continuous structure with the flowable dental material contained in the package.

The invention further provides a relatively easy manufacturing process. In particular, the invention may allow one to package dental material with a reduced number of handling steps. Such a system may, for example, operate with a reduced number of part feeders, if separate pistons and caps are no longer required, for example.

DETAILED DESCRIPTION OF THE DRAWINGS

Figure 1:
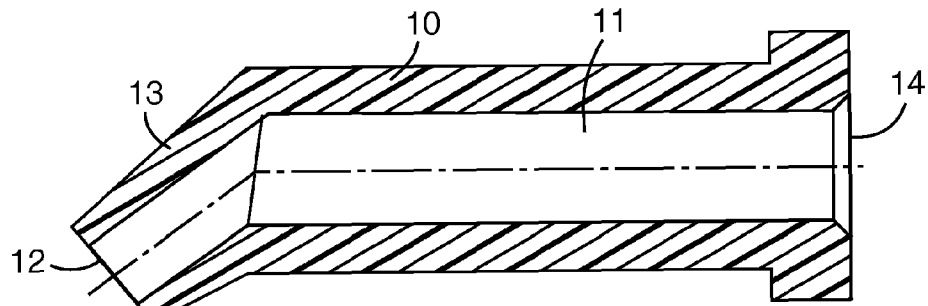
FIG. 1 is a cross-sectional view of a container according to an embodiment of the invention.
Figure 3:
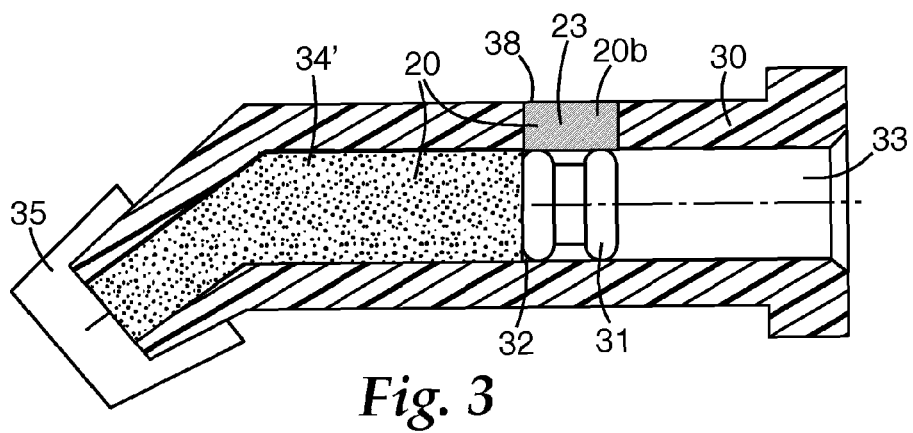
FIG. 3 is a cross-sectional view of a package with a container having a side opening according to an embodiment of the invention.

FIG. 1 shows a container 10 with a chamber 11 and an outlet opening 12. A part of the chamber forms a nozzle 13 which is the section that is inclined with respect to the horizontal part of the chamber 11 as shown in the Figure. The nozzle 13 is arranged at a front end of the chamber 11, and helps for precisely guiding material discharged from the chamber 11 to a desired location. The chamber 11 in this example is of a generally cylindrical shape, however other suitable shapes may be used, like for example one having a cross-section that resembles an oval or a "D". The interior of the nozzle 13 may have a smaller cross-sectional area than the chamber 11 to allow more precise dispensation of the material that may be held in the chamber 11. The chamber 11 further has a rear opening 14 at the rear end of the container, through which, for example, the material may be filled into the container 10 and/or a piston may be inserted into the chamber 11. The chamber 11 may also be filled with material through the nozzle 13, or through an opening in the side of the chamber, as shown in FIG. 3, or in any other suitable manner.

Figure 2:
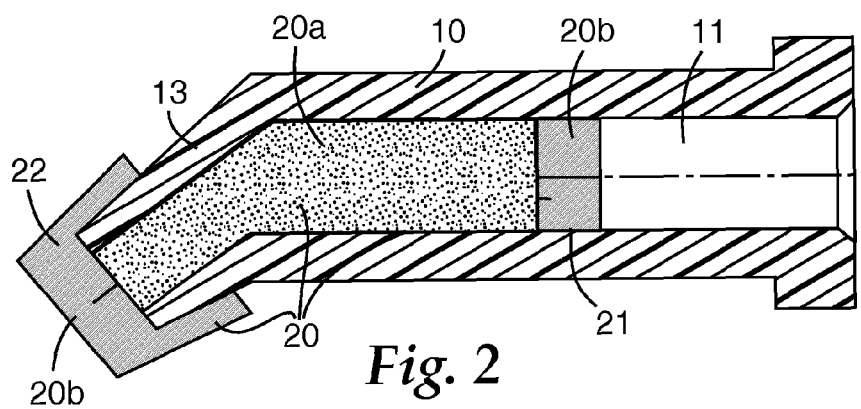
FIG. 2 is a cross-sectional view of a package filled with a flowable dental material, comprising a cap and a piston of a non-flowable dental material according to an embodiment of the invention.

FIG. 2 shows the container 10 holding a hardenable, flowable material 20 that has a portion of a material 20a and a portion of a material 20b. In the example shown the material 20a is flowable and the material 20b is hardened and therefore non-flowable, with the non-flowable material 20b forming a piston 21 and a cap 22. The non-flowable material 20b and the flowable material 20a are obtainable from the material 20. For example, the flowable material 20a may correspond to the material 20, and the non-flowable material 20b may correspond to a hardened portion of the material 20. For example, the material 20b is a polymerized portion of the material 20 and may be obtained by light-curing a portion of the material 20. Such light curable material may be a dental material like Filtek™ Supreme or Filtek™ Z250, for example, as available from 3M ESPE of Seefeld, Germany.

The cap 22 closes the outlet 12 of the container 10 to prevent air from directly contacting the flowable material 20a that is held within the container 10. The piston 21 hermetically seals the chamber 11 so that the flowable material 20a is disposed between the cap 22 and the piston 21. The container 10 together with the cap 22 and the piston 21 therefore form a package for the flowable material 20a contained in the container, in this embodiment of the invention.

The container 10 is typically made of a plastic material that does not bond (or is treated so that it does not bond) with the material 20b, meaning that the material 20b is displaceable relative to the container 10. In particular the cap 22 and the piston 21 preferably remain movable relative to the container 10. Typically such plastic material may be selected from among polyoxymethylene, polybutadiene terephthalate or polyamide, for example.

The plastic material is preferably also selected so that the non-flowable material 20b remains releasable from the plastic material. The plastic material may also be coated with a lubricant, for example with silicone oil, to facilitate the dispensation of material 20, 20a, and 20b from the container 10. The lubricant may also be incorporated in the plastic material as an additive, for example as provided by the material Kemamide® E Ultra of Chemtura Corporation of Middlebury, Conn.

The cap 22 is designed so that it can be removed from the container 10 for dispensation of material 20a contained in the container 10. The inner configuration of the cap 22 preferably does not include features, such as a significant undercut, that would render the cap difficult to remove from the container. However, the inner configuration of the cap may form a slight undercut or other feature that secures the cap to the container but still allows a user to remove the cap. This is advantageous for avoiding unintentional opening of the container, for example during transport from a manufacturer of the container to a user. One design that allows relatively easy removal of the cap 22 includes a generally conical outer shape of the nozzle 13 with which the cap 22 cooperates. Alternatively the outer shape of the nozzle may be cylindrical.

The piston 21, as shown, is of a cross-sectional shape generally corresponding to the inner shape of the chamber 11. The piston 21 is designed to slide smoothly within the chamber 11 and thereby maintains a seal with the chamber 11, for example when the piston 21 is advanced to dispense material from the container 10. In particular the outer shape of the piston 21 substantially corresponds to the inner shape of the chamber 11, and the length and other characteristics of the piston 21 are selected to prevent the piston 21 from twisting or turning sideways when pressure is applied to the back end of the piston 21.

Figure 3A:
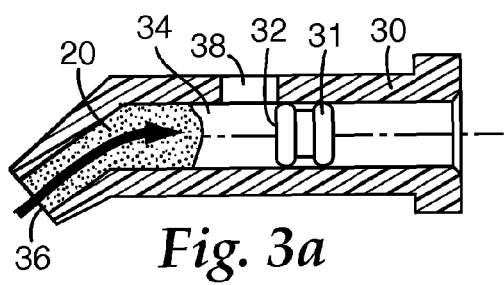
FIGS. 3a and 3b are views of the package of FIG. 3, illustrating steps of a filling method according to an embodiment of the invention.
Figure 3B:
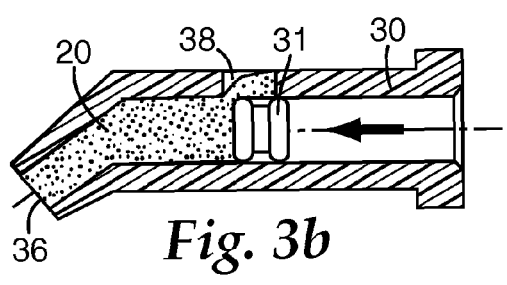

FIG. 3 shows another embodiment of a package comprising a container 30 having a side opening 38 in a side wall. This side opening 38 is closed with a portion of a non-flowable material 20b forming a plug 23. Such embodiment may be advantageous for filling of the chamber 33 of the container 30, in particular to avoid inclusion of air in the chamber 33 during filling and/or during closing of the chamber 33. An exemplary method of filling a container of the embodiment of FIG. 3 is outlined in FIGS. 3a and 3b. FIG. 3a shows nozzle-end filling of the container 30 with the side opening 38 still open. The piston 31 is placed in an initial position in chamber 33 and divides off a sub-chamber 34 from the chamber 33 which is located between the piston front end 32 and the outlet 36. In the initial position, shown in FIG. 3a, the piston 31 leaves the side opening 38 unobstructed. The side opening 38 at this stage serves as a vent for the air that is displaced by the material 20 during filling of the sub-chamber 34. Once the sub-chamber 34 is sufficiently filled to an initial fill level the piston 31 is optionally moved forward as shown in FIG. 3b until the front end 32 of the piston 31 has almost passed the side opening 38. The piston 31 thereby displaces material 20 towards and through the side opening 38 so that the side opening finally is filled with material 20. At this stage the nozzle of the container may be closed, for example by a cap 35 (shown in FIG. 3) or by a filling needle (not shown) that has been used for filling so that the material does not exit through the nozzle.

The person skilled in the art will appreciate that the relationship between the initial position of the piston 31, the initial fill level of the sub-chamber 34 and the size of the side opening may be selected in many variations. In particular the skilled person will appreciate that the relationships among these and other design parameters may be selected so that the amount of material 20 displaced by the piston 31 substantially corresponds to the amount of material required to fill the side opening 38 without overfilling. For example, the piston 31 may initially be placed so that it partially overlaps with the side opening 38, and the sub-chamber 34 may be completely filled. The amount of material between the piston front end 32 and the front-most boundary of the side opening 38 may then substantially correspond to the amount of material required for filling the side opening 38.

In the example of FIG. 3 the plug 23 is shown which is obtained by hardening the material 20 that has been displaced into the opening to become non-flowable material 20b. The plug 23 may be mechanically retained within the side opening (not shown). This means that the material 20b itself may not be bonded to the container 30, but an undercut in or adjacent the side opening 38 may hold material 20b in place. The plug 23 may be hardened, for example light-cured in a direction from the exterior towards the interior of the container 30. The plug 23 is further schematically shown as having precise boundaries that are aligned with boundaries of the container, however, the plug may have a non-uniform shape. In particular the interior shape of the plug may be formed as result of the depth to which the light used for curing the material has penetrated into the material.

The piston 31 defines with its front end 32 a sub-chamber 34' that has a reduced volume relative to the sub-chamber 34 defined by the piston 31 in an initial position (shown in FIG. 3a). The side opening 38 and the piston 31 may also be located farther towards the rear end of the container. The sub-chamber 34' is filled with a flowable material 20a and is preferably devoid of air. The container is closed by a cap 35 so that the material 20a is sealed in the sub-chamber 34'. The piston 31 and the cap 35 in this example are preferably made of a plastic material other than the material 20, 20a and 20b, for example made of polypropylene, polyamide polyoxymethylene, polybutadiene terephthalate. The piston 31 and the cap 35 may therefore be pre-manufactured, for example, by injection molding and assembled with the container.

The plug 23 may be arranged in a certain position in the container 30 to prevent it from having to bear significant pressure from the flowable material 20b during dispensation from the container 30. In the example shown in FIG. 3, the plug 23 is arranged so it is only exposed to a small portion of the flowable material 20a. In other words, the majority of the plug 23 is located outside the sub-chamber 34' so that the pressure in the flowable material 20a only affects a small area of the plug 23. This helps to reduce the force necessary to retain the plug 23 in the side opening 38 and helps to avoid leakage through the side opening 38 that may be caused by a plug that has loosened in response to the material pressure. The side opening 38 in the side wall of the container may be generally small, for example, in case the opening is mainly designed to allow air to escape from the sub-chamber 34. Therefore the plug 23 formed within the side opening 38 would have a relatively small area that faces the material in the sub-chamber 34', and the pressure applied to the relatively small area would also cause generally low forces on the plug 23.

Although the embodiment shown in FIG. 3 shows only the plug 23 of a non-flowable material the embodiment may generally allow to form one or more such plugs or additionally one or more caps and/or pistons to be formed from hardening the flowable material.

The embodiments shown in FIGS. 2 and 3 provide advantages in manufacturing containers that are filled with a flowable material. In particular, such embodiments allow the containers to be filled and to create a closure without the need for additional parts. Therefore, assembly of separate closure parts is also unnecessary. Furthermore, these embodiments can allow for methods for filling of the container substantially devoid of air.

Another advantage is provided by the embodiments of FIGS. 2 and 3, in that they allow a user to recognize how the material 20 in the container looks, because a non-flowable portion of the material contained in the container 10/30 forms an outer part of the package that is visible for a user. For many applications it is important for the user of a package of the type described in this specification to know about such optical characteristics before the material actually has been applied to and allowed to cure in a desired location. For example, in the field of dentistry a dentist typically selects a filling material so that its color essentially matches the color of a tooth that is in need of a restoration. In this case the color of the material is important, but so is its translucency, because human teeth generally exhibit both properties.

The closures of the present invention, such as cap 22 of the package shown in FIG. 2 and the plug 23 in the package shown in FIG. 3, indicate on an outside of the package the optical characteristics of the material after it has been hardened. This is advantageous because the non-flowable material may have a different optical characteristic than the flowable material it is obtained from, so that the preparation and subsequent observation of a sample by the user can be avoided. Furthermore, unnecessary opening of packages may be prevented because the optical characteristic of the material is represented by the package itself.

Figure 4:
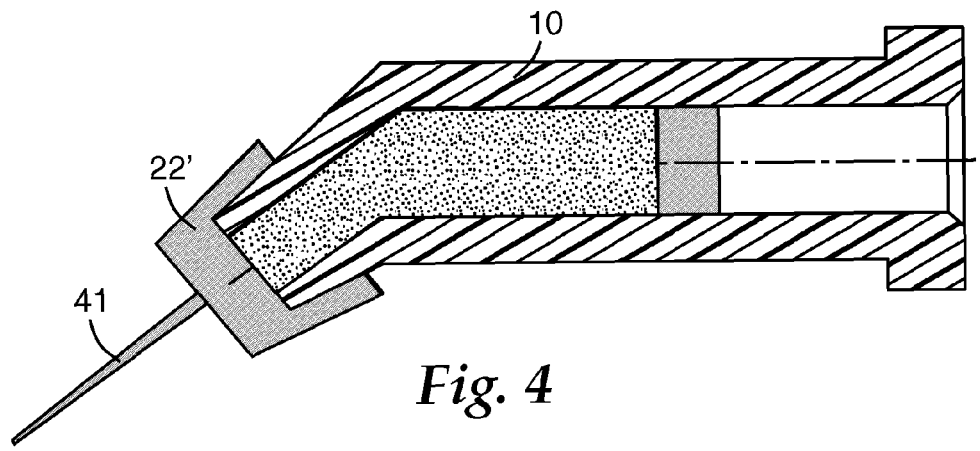
FIG. 4 is a cross-sectional view of a package having a cap with an indicator according to an embodiment of the invention.
Figure 4A:
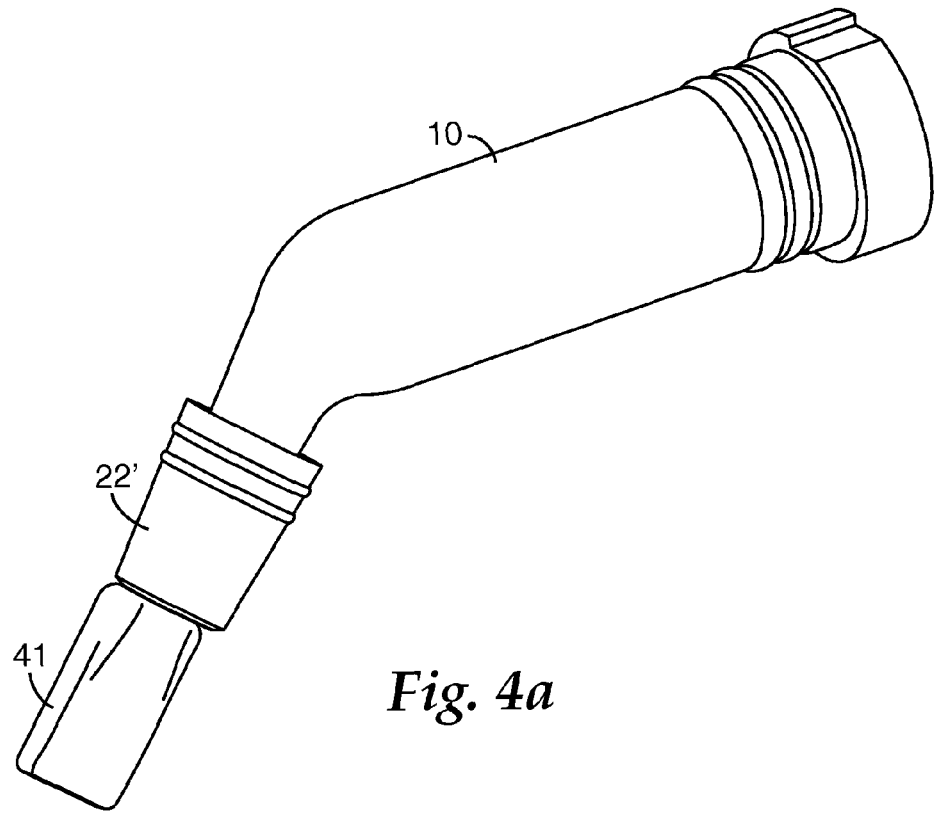
FIG. 4a is a perspective view showing a package having a cap with a tooth shaped indicator according to an embodiment of the invention.

FIG. 4 shows another embodiment which provides a user with the optical characteristics of the material. The package shown in FIG. 4 has a cap 22' with an extension 41 that tapers in a direction away from the container 10. When that cap 22' is made from the same material as the contents of the container, then a user of such a package can easily recognize both the color and the translucency of the material. This is because the extension 41 preferably has thinner and thicker portions (for example, thinner toward its far end, and thicker toward its near end) so that it provides an indication of the color and translucency properties of the material for different material thicknesses. Preferably the extension 41 is at least partially made relatively thin so that its translucency characteristics can be easily recognized, for example by observing it under normal daylight conditions. In the example shown in FIG. 4, the extension 41 is made generally disc shaped, however other shapes are included in the scope in this specification, especially shapes that resemble one or more human teeth (see for example FIG. 4a). The extension or the container or both may also comprise indicia that indicate a color and/or translucency of the material when measured according to a standard.

Figure 5A:
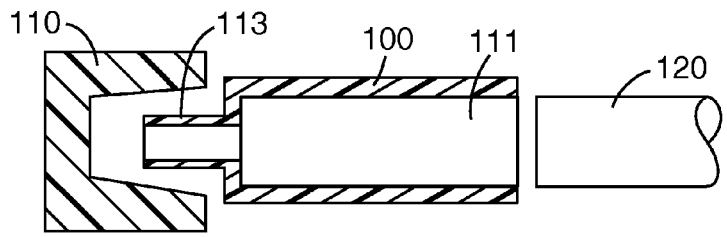
FIGS. 5a-5e illustrate a method of making a package according to an embodiment of the invention.
Figure 5B:
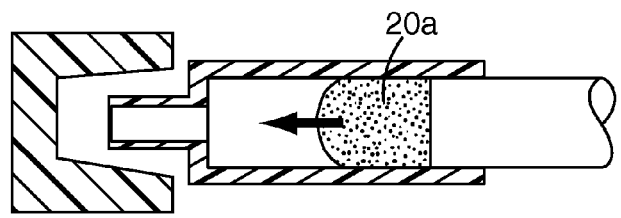
Figure 5C:
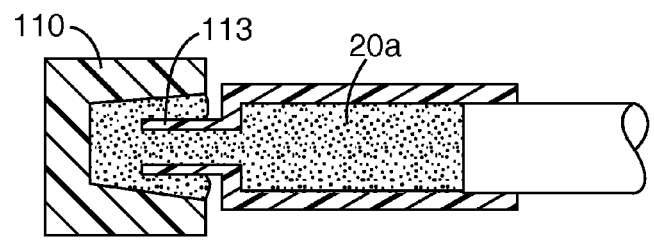
Figure 5D:
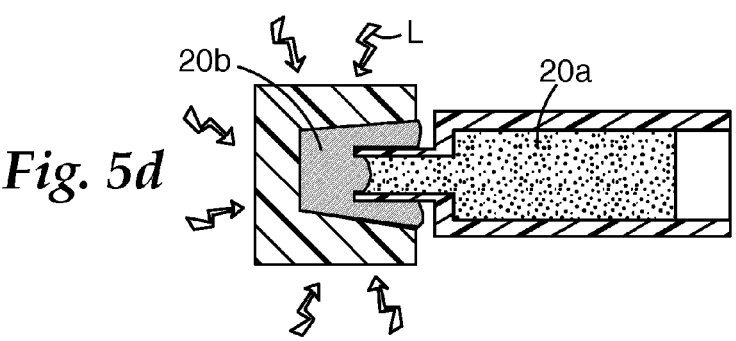

FIGS. 5a to 5e schematically show an exemplary manufacturing process for a package according to the certain embodiments of the invention. The steps shown may, where appropriate, be performed in a different order than shown, divided into multiple steps, or merged into a single step. FIG. 5a shows a container 100, a mold 110 and a filling tube 120 in an initial state in which the container 100 is empty. The mold 110 is placed at the front end of the container 100 close to the nozzle 113, and the filling tube 120 is positioned at the rear end of the container 100. In FIG. 5b the filling tube 120 is inserted in the chamber 111 of the container 100 and the filling process has started. The filling tube 120 may be sized or otherwise configured to seal the chamber 111 during filling to prevent material from bypassing the filling tube 120 and flowing out of the rear end of the container 100. The container 100 is filled with a material 20a, which flows from the filling tube 120 towards the front end of the container 100. In FIG. 5c the container 100 is completely filled and a portion of the material 20a has been extruded through the nozzle 113 into the mold 110, thus filling a gap between the exterior of the nozzle 113 and the interior of the mold 110. In FIG. 5d the material 20a in the gap between the nozzle 113 and the mold 110 is hardened and has become a material 20b. In this example, the material is cured by light, for example by UV- or blue light, as indicated by light flashes "L". The mold may be transparent, for example made of glass, so that light can pass through it. This allows a light source for curing of the material 20a to be arranged outside of the mold. Further it allows irradiation of large areas of the material 20a to eventually facilitate fast and homogeneous curing. Instead of a transparent mold an opaque mold may be used and the light for curing may be applied to the material in the gap between the container and the mold only. The mold may be configured to provide a cap of any suitable size and shape, in particular to provide a cap as shown in FIG. 4. The container 100 is preferably opaque to the light used for hardening of the material.

Figure 5E:
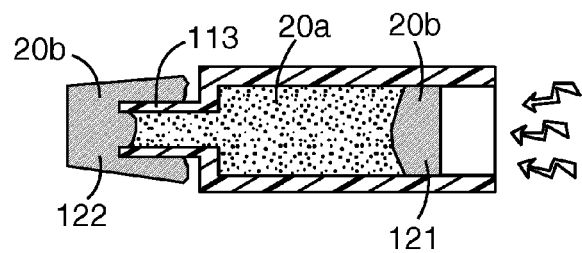

In FIG. 5e the mold has been removed from the material 20b, which now forms a cap 122 sealing the container 100 at its nozzle 113. Optionally, through the open rear end of the container another portion of the material 20a is rendered non-flowable, for example cured by light, so that a piston 121 is formed of non-flowable material 20b. As shown in FIGS. 5a to 5e, the package is filled and sealed, and closures (a cap and a piston) for the package have been provided. This method and others similar to it may reduce the number of parts that have to be assembled, such as the plug and the cap, which may save manufacturing costs. Even when rather expensive material is used for filling the package, these methods may be economical because the material cost may be lower than the cost arising from normal capping and plug insertion operations.

In a manufacturing process for a package according to a particular embodiment of the invention the container may be filled with at least a first portion of a flowable dental material of which a first sub-portion may be hardened to form a piston which is then used to force a second sub-portion of the dental material out through the nozzle. The second sub-portion of material may then be hardened to form a closure, for example a cap. In this embodiment the first and second sub-portions preferably correspond to a predetermined second portion of the flowable dental material. The container according to such particular embodiment may be front-end filled, through the nozzle, and as soon as the container is filled with an amount of material sufficient to form the piston the piston may be formed by hardening material in the container. The material may for example be hardened through the open rear end of the container which may be accessible during front-end filling. The piston therefore may be pushed towards the rear end of the container by material subsequently filled in the container. This may be advantageous because moving of the piston after hardening may result in a relatively low break away force of the piston when the container is first used to dispense material. This is, because a piston that is formed by hardening and left in place may relatively precisely fit the shape of the inside of the container and therefore form a certain adherence to the container so that the force to move it out of this position may be relatively high. The container according to this particular embodiment may, however, also be filled completely or overfilled before a sub-portion of the material is hardened to form the piston.

In an optional embodiment of the manufacturing process of the invention the closure of the invention, such as a cap, a plug and/or a piston, are made independently from the filling process. Such closure may be made, for example, in a manufacturing process that is separate from the filling process and assembled to the container prior to, during or after filling the container.

Figure 6A:
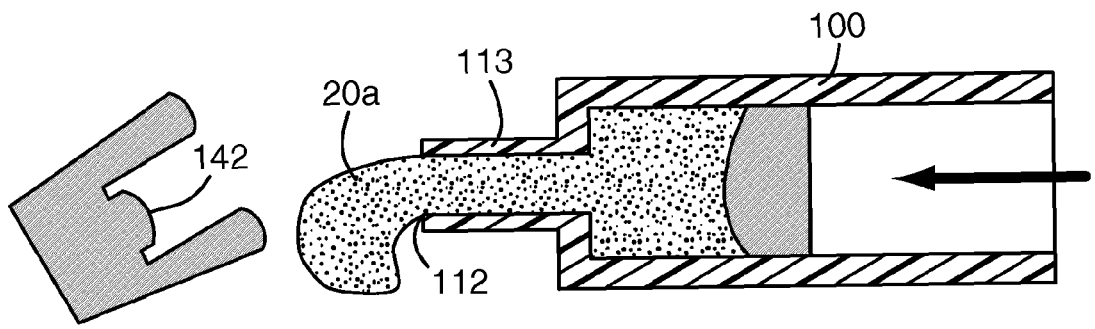
FIG. 6a is a cross-sectional view of an opened package from which material has been extruded according to an embodiment of the invention.
Figure 6B:
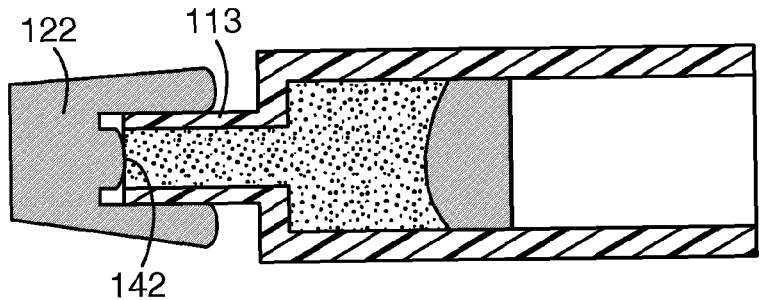
FIG. 6b is a cross-sectional view of a re-closed package from which material has been extruded according to an embodiment of the invention.

FIGS. 6a and 6b show an embodiment of the invention in use. In FIG. 6a the cap 122 has been removed and a portion of the material 20a is being extruded from the container 100, whereas in FIG. 6b the container 100 is being re-closed. The cap 122 has a pin 142 which was initially accommodated within the nozzle 113, thus plugging the outlet 112. Such a pin 142 may form as a result of the hardening step of the material that forms the cap 122. The pin 142 may also be intentionally created, for example by making at least a portion of end of the nozzle of a transparent plastic material, in cases in which the material in the container is a light curable material. Generally the degree of hardening, in particular the depth to which the material hardens, may be controlled by using light of a certain intensity, wavelength or by exposing the material to the light over a certain period of time. It may also be possible to vary the light intensity, the wavelength and/or the exposure time of the material. The pin may help to seal the container so that the material 20a contained therein is better protected from contact with air outside of the container. As shown in FIG. 6b, the pin 142 may not penetrate into the nozzle 113 when the container is re-closed after extruding the material. This is because penetration of the pin 142 would require the material in the nozzle 113 to be pushed back into the container 100, which may be undesirable because of the high forces required, or because the material displaced by the cap 122 may contaminate the interior of the cap 122. Therefore the cap 122 may be designed so that it can be easily used for re-closing the container 100 without inserting the pin back into the nozzle 113. This is provided by a rim of the cap 122 that projects ahead of the end of the pin so that the projecting part of the rim can be mated with the nozzle.

Figure 7:
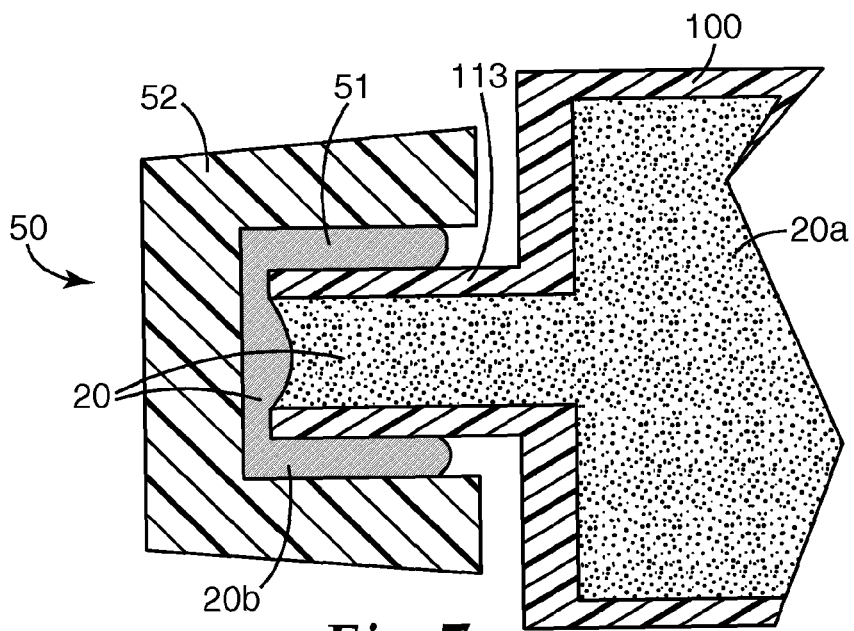
FIG. 7 is a cross-sectional view of a front of a package with an alternative cap according to an embodiment of the invention.

FIG. 7 shows an alternative embodiment of a cap 50. The cap 50 comprises an outer part 52 and an inner part 51. The outer part 52 is preferably made of a plastic material like polyoxymethylene, polybutadiene terephthalate or polyamide, for example, from which the outer part may be pre-manufactured. The inner part 51 is made of a material 20b which is a hardened and therefore non-flowable portion of the material 20. The material of the outer part 52 may be selected so that it bonds or sticks with the non-flowable material. Such embodiment may be made by pre-assembly of the container 100 and the outer part 52. When the container is filled with material 20, a portion of the material may be displaced into a gap between the outer part 52 and the nozzle 113 of the container. The material 20 in the gap may then be hardened, for example light cured, so that it forms the inner part 51 of the material 20b which seals the container 100. The outer part 52 may be made of a transparent material to provide easy light curing of the material 20. The recess of the outer part 52 may have retaining elements (not shown) for anchoring the outer part 52 to the inner part 51. For example the outer part 52 may have protrusions within the recess that project into the inner part 51 to lock both parts together. Such protrusions may further be used to pre-assemble the outer part 52 with the container 100 prior to filling. This embodiment may be advantageous for providing a cap having relatively high mechanical stability, which at the same time provides a good seal for the container. This may be achieved because the outer part 52 may be of a more robust material than the material in the container. Further, because the material 20 is preferably initially flowable, it may precisely conform to the structure of the gap between the outer part 52 and the nozzle 113 and therefore may provide a good seal therebetween.

Figure 8:
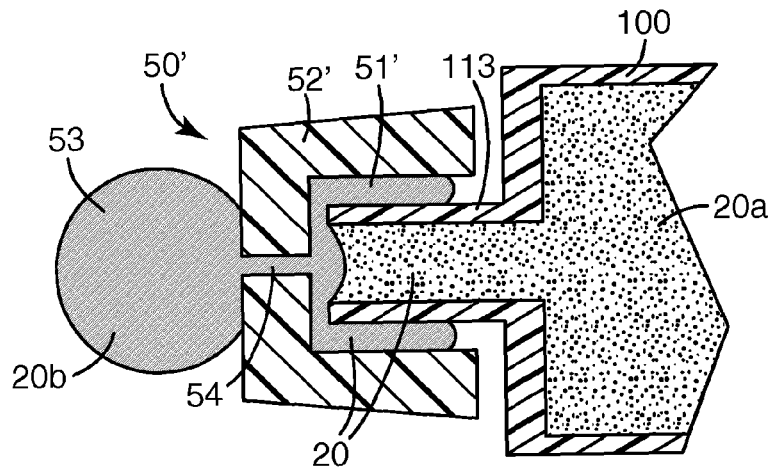
FIGS. 8, 8a are cross-sectional views of a front of a package with an alternative cap in two stages of manufacturing according to an embodiment of the invention.
Figure 8A:
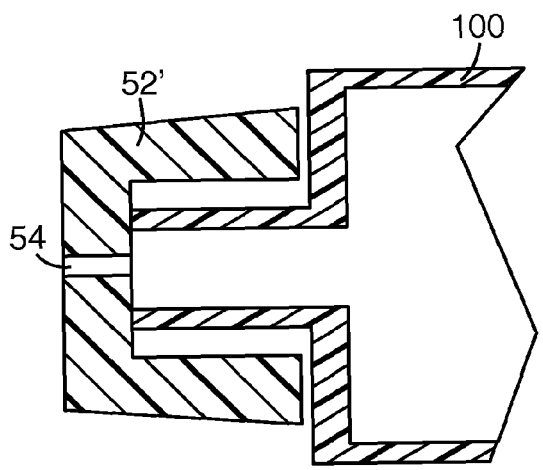

Another embodiment is shown in FIG. 8 which has a design similar to that shown in FIG. 7. However cap 50' has a bore 54 in its front side from which material 20 may be extruded during filling of the container 100. For manufacturing, the outer part 52' may be placed onto the nozzle 113 of the container so that the outer part is in contact with the front-most part of the nozzle (see FIG. 8a). During filling the material 20 in a first step may be extruded through bore 54 to form the extension 53, which in this example is disc shaped but may also be tooth-shaped or shaped in any suitable form. For forming the extension 53, the material extruded through the bore 54 may be received in a mold that connects with the outer part 52' (not shown). In a second step the outer part 52' may be spaced away from the nozzle so as to provide a gap between the outer part 52' and the nozzle 113 which is subsequently filled with the material 20. Finally the material 20 in the mold and in the gap may be hardened, for example light cured, to form the material 20b. This embodiment may be advantageous for easy manufacturing of an extension 53 to provide the color and the translucency indications to a user. It may further provide good mechanical stability of the cap 50' because the outer part 52' may reinforce the inner part 51' sealing the container 100. The extension 53 of this embodiment preferably tapers off toward its boundaries so that it provides the color and/or translucency gradient of the material 20b as described above.

Figure 9:
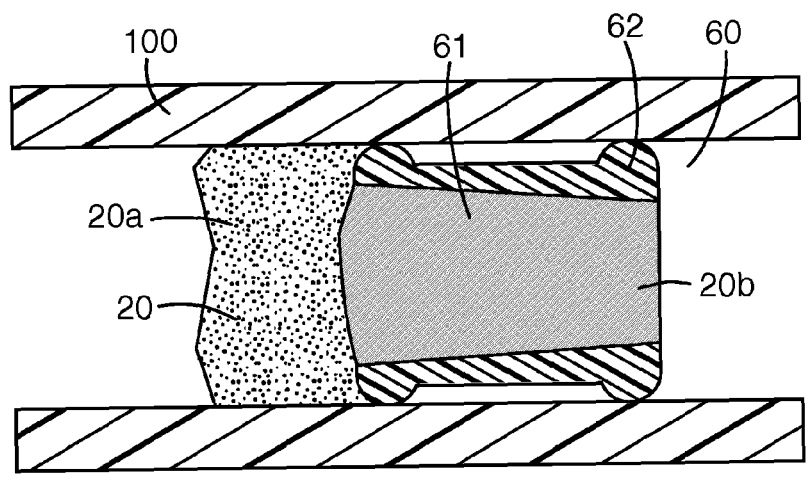
FIG. 9 is a cross-sectional view of a section of a package with a piston according to an embodiment of the invention.

The embodiment of FIG. 9 shows a piston 60 having an outer part 62 and an inner part 61. The outer part 62 may be made of a plastic material as mentioned for the outer part 52/52' of certain previous embodiments. The inner part 61 is made of material 20b which is obtained by hardening, for example light curing, of a portion of material 20. This embodiment may be advantageous for providing a piston having good sliding properties and for providing a piston that allows for the escape of air from within the chamber. This may be done by first disposing the outer part 62 of the piston 60 in the container 100, and then filling the container 100 through the piston 60 or through the nozzle or another opening (not shown in FIG. 9). After filling the chamber the material within the piston 60 may be hardened to contain the material 20a within the container. As shown, the inner part 61 of the piston may be conical with the wider end oriented toward the front end of the container so that the inner part 61 is retained within the outer part 62 when the piston 60 is used for extruding material from the container.

The embodiments described in this specification may be adapted for front-end filling (filling from the nozzle end) or back-end filling. In case the container of any embodiment has a side opening, filling through the side opening may be possible. All embodiments described may further be single dose packages, meaning filling with a single dose of material and once used to be disposed. Single dose packages are typically those that have from approximately 50 mg to approximately 500 mg of material, or from approximately 150 mg to approximately 350 mg of material, so that minimal material is left in the package after a user has dispensed enough of the material to, for example, restore a single tooth.

The invention claimed is:

1. A package comprising a container and a dental material, the container having an opening and containing a flowable portion of the dental material, wherein the opening is closed by a closure member that is formed by a non-flowable portion of the dental material, and wherein the closure member forms an indicator.

2. The package of claim 1, wherein the closure member is a cap.

3. The package of claim 1, wherein the opening is arranged within a side wall of the container and the closure member is a plug.

4. The package of claim 1, wherein the closure member is a piston.

5. The package of claim 1, wherein the flowable portion and the non-flowable portion are substantially continuous.

6. The package of claim 1, wherein the flowable portion and the non-flowable portion form a transition zone between one another.

7. The package of claim 1, wherein the indicator provides the color shade of the material.

8. The package of claim 1, wherein the indicator has a light transmissive portion.

9. The package of claim 1, wherein the indicator is integrally formed with the closure member.

10. The package of claim 1, wherein the indicator in shape resembles a human incisor.

11. The package of claim 1, wherein the dental material is a light curable dental material.

12. The package of claim 1, adapted for containing a single dose amount of flowable dental material.

13. A kit comprising a plurality of packages, wherein each of packages comprises a container and a dental material, the container having an opening and containing a flowable portion of the dental material, wherein the opening is closed by a closure member that is formed by a non-flowable portion of the dental material.

14. The kit of claim 13, comprising a plurality of packages having a material of a different color shade.

* * * * *